(12) United States Patent
Negoro et al.

(10) Patent No.: US 6,803,349 B2
(45) Date of Patent: Oct. 12, 2004

(54) HETEROCYCLIC RING-CONTAINING COMPOUND AND A LUBRICANT COMPOSITION USING THE SAME

(75) Inventors: Masayuki Negoro, Kanagawa (JP); Kensuke Morita, Kanagawa (JP); Ken Kawata, Kanagawa (JP)

(73) Assignee: Fuji Photo Film Co., Ltd., Minami-Ashigara (JP)

( * ) Notice: Subject to any disclaimer, the term of this patent is extended or adjusted under 35 U.S.C. 154(b) by 0 days.

(21) Appl. No.: 10/253,420

(22) Filed: Sep. 25, 2002

(65) Prior Publication Data

US 2003/0207774 A1 Nov. 6, 2003

(30) Foreign Application Priority Data

Sep. 25, 2001 (JP) .......................................... 2001-291080

(51) Int. Cl.$^7$ ................... C10M 133/42; C07D 251/38; C07D 251/48; C07D 251/54
(52) U.S. Cl. .................... 508/258; 508/257; 544/197; 544/204; 544/208; 544/213; 544/215; 544/217; 544/218; 544/219
(58) Field of Search ............................... 508/257, 258; 544/204, 208, 213, 215

(56) References Cited

U.S. PATENT DOCUMENTS

| | | | |
|---|---|---|---|
| 3,156,690 A | * 11/1964 | Dexter et al. | 544/211 |
| 3,378,490 A | * 4/1968 | Hotten | 508/258 |
| 3,530,127 A | * 9/1970 | Biland et al. | 544/219 |
| 4,038,197 A | * 7/1977 | Caspari | 508/257 |
| 4,906,751 A | * 3/1990 | Schneider | 544/213 |
| 5,032,301 A | 7/1991 | Pawloski et al. | |
| 5,037,568 A | * 8/1991 | O'Neil et al. | 508/258 |
| 5,433,873 A | 7/1995 | Camenzind | |
| 5,507,963 A | * 4/1996 | Wolf | 508/258 |
| 5,639,717 A | * 6/1997 | Berlowitz et al. | 508/257 |
| 6,284,717 B1 | * 9/2001 | Crane et al. | 508/258 |
| 6,528,460 B2 | * 3/2003 | Kawata et al. | 508/258 |

FOREIGN PATENT DOCUMENTS

EP 0 398 843 A1 11/1990

OTHER PUBLICATIONS

EPO Search Report dated Dec. 30, 2002 in EP Application No. 02021377.3–2117.
Peter Timmerman et al, Ag $^+$Labeling: A Convenient New Tool for the Characterization of Hydrogen–Bonded Supramolecular Assemblies by MALDI–TOF Mass Spectrometry, Chem. Eur. J. 2000, vol. 6, No. 22, pp 4104–4115.
Frank Würthner et al, "Hydrogen bond directed formation of liquid–crystalline merocyanine dye assemblies," Chem. Commun., 2001, vol. 21, pp 2260–2261.

* cited by examiner

Primary Examiner—Ellen M. McAvoy
(74) Attorney, Agent, or Firm—Burns, Doane, Swecker & Mathis, L.L.P.

(57) ABSTRACT

A heterocyclic ring-containing compound represented by the following formula (1). In the formula, D represents a heterocyclic ring residue having a 5- to 7-membered ring structure and substituted with (m+n) of substituents, X represents a divalent linking group consisting of a single bond, $NR^3$ group ($R^3$ represents a hydrogen atom or an alkyl group having 1–30 carbon atoms), an oxygen atom, a sulfur atom, a carbonyl group, a sulfonyl group or a combination thereof, $R^1$ represents an alkyl group, an alkenyl group, an alkynyl group, an aryl group or a heterocyclic group, which may be substituted or unsubstituted, $R^2$ represents a halogen atom, a hydroxy group, an unsubstituted amino group, a mercapto group, a cyano group, a sulfide group, a carboxy group or salt thereof, a sulfo group or salt thereof, a hydroxyamino group, a ureido group or a urethane group, m represents 1 or 2, and n represents an integer of 1 or larger. There is provided a novel heterocyclic ring-containing compound showing superior lubricant performance.

22 Claims, No Drawings

HETEROCYCLIC RING-CONTAINING COMPOUND AND A LUBRICANT COMPOSITION USING THE SAME

TECHNICAL FIELD

The present invention relates to a novel heterocyclic ring-containing compound, more precisely, a novel heterocyclic ring-containing compound utilized for a lubricant to be supplied between surfaces sliding with mechanical friction and so forth.

RELATED ART

The performance required for a lubricant is that it can reduce friction coefficient of surfaces sliding with mechanical friction within a wide temperature range and wide pressure range, and such an effect should be maintained as long as possible. Further, a lubricant is required not only to have an effect of improving lubricity between members sliding with friction, but also to be able to impart wear resistance to the members sliding with friction themselves. The effect of lubricant such as engine oil for reducing frictional coefficient between members sliding with friction and a longer lifetime thereof directly lead to improvement in fuel consumption of mechanical driving, i.e., energy saving. Since a longer lifetime of engine oil makes possible not only reduction of the amount of waste oil but also reduction of exhausted $CO_2$, it is preferred also in view of compatibility for environment, which is noted in recent years. Further, among sliding surfaces of industrial machines, if a conventional lubricant or grease is used for bearings or gears, which slide under especially severe frictional conditions, the lubricant may suffer from breakage of lubricant film or cause seizing when the lubricating conditions become severer, and thus a desired low friction coefficient may no longer be obtained due to wearing out damages. As a result, reliability of apparatuses may be degraded, and especially when a smaller apparatus is used, the friction conditions of sliding surfaces tend to become severer, which makes it difficult to use a smaller apparatus. Therefore, there is desired a energy-saving type lubricant that does not cause wearing out or seizing even under severe conditions and thereby enables improvement of reliability of apparatuses and contributes to use of a smaller apparatus.

Furthermore, in recent years, a lubricant supplied to surfaces of high density magnetic recording media, sliding surfaces or rotating members of micromachines and so forth is required that it can maintain such performances as mentioned above with an extremely small amount. That is, there is desired a lubricant that can cover a friction surface with a minimum amount to reduce friction coefficient of sliding surfaces and improve wear resistance, and can maintain such effects as long as possible. In order to respond to this requirement, a lubricant is inevitably required to have a property that it can readily form a uniform and smooth thin membrane.

Meanwhile, as lubricants, there have been conventionally used those containing lubricating base oil as a main component and blended lubricating aids such as organic compounds. As a typical example of the lubricating aids, diorganodithiocarbamic acid can be mentioned, and it is known that metal salts thereof show various functions as antioxidant, wear resistant agent, corrosion inhibition additive and so forth for lubricants. For example, the zinc salt disclosed in U.S. Pat. No. 4,278,587, antimony salt disclosed in U.S. Pat. No. 4,290,202, molybdenum salt disclosed in U.S. Pat. No. 4,360,438 and metals salts such as nickel, copper, cobalt, iron, cadmium and manganese salts disclosed in International Patent Publication in Japanese (Kohyo) No. 9-508156 have a remarkable effect that they can maintain low friction property and low wearing property of sliding surfaces even under severe conditions. In recent years, organic molybdenum compounds are particularly noted as lubricating aids. Organic molybdenum compounds are noted as materials that still show superior performances including wear resistance, extreme pressure resistance (withstand load property), low friction characteristics and so forth even when sliding members of mechanical apparatuses are moved under severe friction conditions caused by high temperature, high speed or low speed, high load, use of small size and so forth, and can effectively exert the lubricating performance under a pressure higher than ordinary pressure of fluid lubrication condition, i.e., a boundary lubrication condition.

However, it is known that the effect becomes more significant if zinc dithiophosphate is used together with the organic molybdenum compounds compared with a case of using the organic molybdenum compounds alone. Muraki, M., et al reported a mechanism that when a thin membrane of zinc dithiophosphate is formed on frictional surfaces, molybdenum dithiocarbamate or molybdenum dithiophosphate adsorbs on it, react with it and degrade to form a thin membrane of a mixture of molybdenum sulfide and molybdenum oxide (Tribologist, vol. 38, p. 10 (1993)). Arai, K., et al investigated elemental composition of surface portion of member sliding with friction along the depth direction by X-ray photoelectron spectroscopy (XPS) to confirm that molybdenum, sulfur and oxygen derived from molybdenum dithiocarbamate gradually decreased from the surface and iron elements increased conversely, and explained that low friction coefficient and wear resistance were obtained by formation of a composite film resulting from a reaction of metal iron on the sliding surface with molybdenum (Tribologist, vol. 44, p. 46 (1999)). Further, Kikuchi, T., et al. described that, besides zinc dithiophosphate, sulfur compounds such as sulfurized oil and fat, sulfurized olefin and sulfurized phenate also showed a synergistic effect with molybdenum dithiocarbamate for providing low friction property (JSAE Paper, 9537538 (1995)).

Although molybdenum dithiocarbamate is an outstanding material that exerts superior lubricating effect even under severe frictional conditions, a lubricant oil using it contains significant amounts of heavy metals such as molybdenum and zinc, sulfides that are easily oxidized to form sulfur oxide, which adversely affects not only the lubricating oil but also sliding members themselves as well as environment, and phosphoric acid, which eutrophicates rivers and the sea, and it is clearly unfavorable in view of compatibility for environment. Furthermore, the molybdenum oxide/molybdenum sulfide coating films formed on sliding surfaces are gradually shaved off by friction to newly form coating films, and therefore if either of the organic molybdenum compound and organic zinc compound that serve as sources of the coating films is depleted, the effect will be lost abruptly. On the other hand, if the amounts of the organic molybdenum compound and organic zinc compound are increased, by-products produced by shaving of the coating films increase in the system and adversely affect the apparatus itself comprising the sliding members. Therefore, increase of amounts of the compounds is not effective, and in fact, the effects such as improvement in fuel consumption brought by a longer lifetime of lubricant cannot be expected so much in a system utilizing the aforementioned organic molybdenum compound.

As described above, as conventional lubricants, there have not been provided yet any material that contains no environmentally harmful substances and environmental-polluting substances such as heavy metal elements, phosphate compounds and sulfides, exhibits superior performances as a lubricant, and can maintain the performances as a lubricant for a long period of time.

SUMMARY OF THE INVENTION

The present invention was accomplished in view of the aforementioned various problems, and its object is to provide a novel heterocyclic ring-containing compound, in particular, a novel heterocyclic ring-containing compound that shows superior lubricating performance not only in a state that it is mixed with conventional lubricant base oil, but also in a state that it is not mixed with lubricant base oil.

As an embodiment of the present invention, there is provided a heterocyclic ring-containing compound represented by the following formula (1).

Formula (1)

In the formula, D represents a heterocyclic ring residue having a 5- to 7-membered ring structure and substituted with (m+n) of substituents, X represents a divalent linking group consisting of a single bond, $NR^3$ group ($R^3$ represents a hydrogen atom or an alkyl group having 1–30 carbon atoms), an oxygen atom, a sulfur atom, a carbonyl, a sulfonyl or a combination thereof, $R^1$ represents an alkyl group, an alkenyl group, an alkynyl group, an aryl group or a heterocyclic group, which may be substituted or unsubstituted, and $R^2$ represents a halogen atom, a hydroxy, an unsubstituted amino, a mercapto, a cyano, a sulfide, a carboxy or salt thereof, a sulfo or salt thereof, a hydroxyamino, a ureido or a urethane. m represents 1 or 2, and n represents an integer of 1 or larger. When m and n are 2 or larger, 2 or more of X, $R^1$ and $R^2$ may be identical to or different from each other or one another, respectively.

As another embodiments of the present invention, there are provided heterocyclic ring-containing compounds represented by the following formulas (2) to (8).

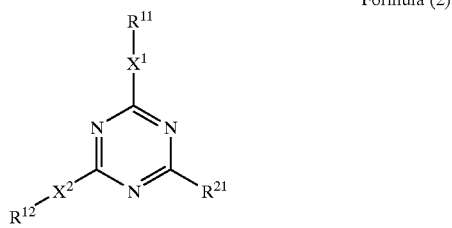

Formula (2)

In the formula, $X^1$ and $X^2$ each independently represent a divalent linking group consisting of a single bond, $NR^3$ group ($R^3$ represents a hydrogen atom or an alkyl group having 1–30 carbon atoms), an oxygen atom, a sulfur atom, a carbonyl, a sulfonyl or a combination thereof (preferably a sulfur atom or an imino (—NH—), more preferably imino). $R^{11}$ and $R^{12}$ each independently represent an alkyl group, an alkenyl group, an alkynyl group, an aryl group or a heterocyclic group, which may be substituted or unsubstituted, and $R^{21}$ represents a halogen atom, a hydroxy, an unsubstituted amino, a mercapto, a cyano, a sulfide, a carboxy or salt thereof, a sulfo or salt thereof, a hydroxyamino, a ureido or a urethane (preferably a halogen atom).

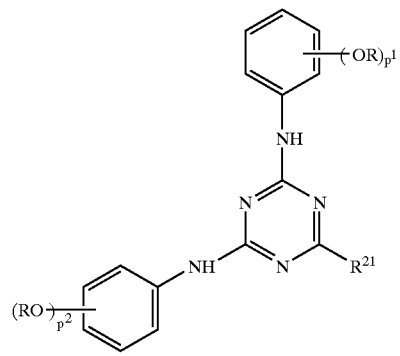

Formula (3)

In the formula, R represents an alkyl group having 8 or more carbon atoms, an oligoalkyleneoxy group having 4 or more carbon atoms or a perfluoroalkyl group having 2 or more carbon atoms, $R^{21}$ represents a halogen atom, a hydroxy, an unsubstituted amino, a mercapto, a cyano, a sulfide, a carboxy or salt thereof, a sulfo or salt thereof, a hydroxyamino, a ureido or a urethane, and $p^1$ and $p^2$ each independently represent 1 or 2.

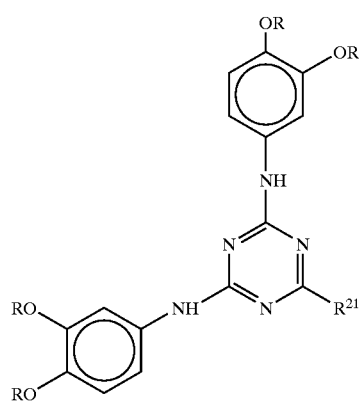

Formula (4)

In the formula, R represents an alkyl group having 8 or more carbon atoms, an oligoalkyleneoxy group having 4 or more carbon atoms or a perfluoroalkyl group having 2 or more carbon atoms, and $R^{21}$ represents a halogen atom, a hydroxy, an unsubstituted amino, a mercapto, a cyano, a sulfide, a carboxy or salt thereof, a sulfo or salt thereof, a hydroxyamino, a ureido or a urethane.

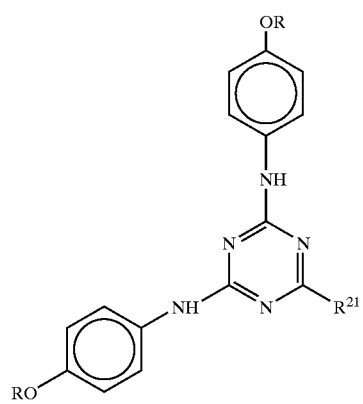

Formula (5)

In the formula, R and $R^{21}$ are each same as those in the formula (3).

Formula (6)

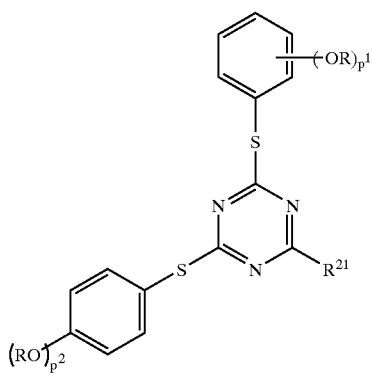

In the formula, R, $R^{21}$, $p^1$ and $p^2$ have the same meanings as defined in the aforementioned formula (3).

Formula (7)

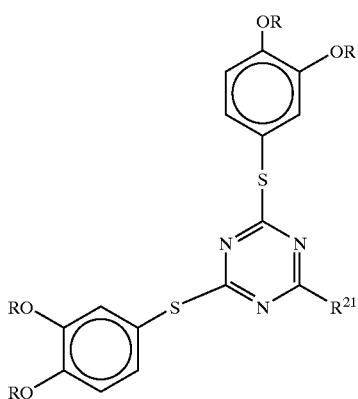

In the formula, R and $R^{21}$ have the same meanings as defined in the aforementioned formula (3).

Formula (8)

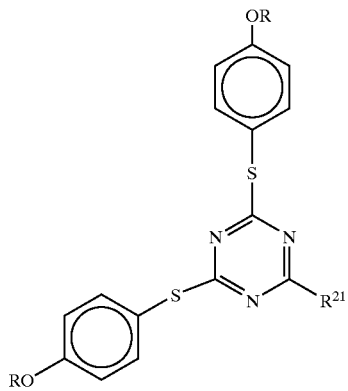

In the formula, R and $R^{21}$ have the same meanings as defined in the aforementioned formula (3).

As embodiments of the present invention, there are provided the heterocyclic ring-containing compound wherein, in the formula (2), at least one of $R^{11}$ and $R^{12}$ contains —(C=O)O—; and the heterocyclic ring-containing compound represented by any one of formulas (3) to (8), wherein at least one of R contains —(C=O)O—.

According to the present invention, there can be provided novel and useful heterocyclic ring-containing compounds, in particular, novel heterocyclic ring-containing compounds that show superior lubricant performance not only in a state that they are mixed with conventional lubricant base oil, but also in a state that they are not mixed with lubricant base oil.

In another aspect of the present invention, this invention relates to use of a heterocyclic ring-containing compound represented by any one of the following formulas (1) to (8) for reducing friction coefficient between sliding surfaces.

DETAILED DESCRIPTION OF THE INVENTION

Hereafter, the present invention will be explained in detail. First, the heterocyclic ring-containing compounds represented by the following formula (1) will be explained.

Formula (1)

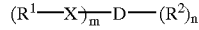

In the formula (1), D represents a heterocyclic ring residue having a 5- to 7-membered ring structure and substituted with (m+n) of substituents. A 5-membered ring or 6-membered ring is more preferred, and a 6-membered ring is the most preferred. Specific examples of such a basic structure include those mentioned in Iwanami Dictionary of Physics and Chemistry (Iwanami Rikagaku Jiten), 3rd Supplemented Edition, published by Iwanami Shoten, Appendix, Chapter 11, Nomenclature of Organic Chemistry, Table 4: Designations of Major Heterocyclic Monocyclic Compounds, p. 1606 and Table 5: Designations of Major Condensed Heterocyclic Compounds, p. 1607. D is preferably an aromatic heterocyclic residue, and it is more preferably an aromatic heterocyclic residue containing a nitrogen atom. In addition, the heterocyclic residue represented by D has (m+n) of substituents, and a hetero atom constituting D may be substituted, or a carbon atom constituting D may be substituted when D represents a heterocyclic residue containing a carbon atom.

In the aforementioned formula (1), X represents a divalent linking group consisting of a single bond, $NR^3$ group, an oxygen atom, a sulfur atom, a carbonyl group, a sulfonyl group or a combination thereof, and $R^3$ represents a hydrogen atom or an alkyl group having 1–30 carbon atoms (including straight and branched alkyl groups). Examples of the divalent linking group consisting of a combination of the groups include oxycarbonyl group, aminocarbonyl group, carbamoyl group, oxysulfonyl group, sulfamoyl group and so forth. When X is a single bond, the heterocyclic residue represented by D is directly substituted with $R^1$. If X is a single bond and $R^1$ is a heterocyclic group, a heterocyclic group such as piperidine may directly bond at a nitrogen atom having a free valence, or the heterocyclic residue may bond even at a hetero atom that does not have a free valence to form an onium salt such as oxonium salt, sulfonium salt and ammonium salt. X is preferably a sulfur atom or $NR^3$ group, and $R^3$ is preferably an alkyl group having 3 or less carbon atoms or a hydrogen atom.

In the aforementioned formula (1), $R^1$ represents an alkyl group, an alkenyl group, an alkynyl group, an aryl group or a heterocyclic group, which may be substituted or unsubstituted. The alkyl group represented by $R^1$ preferably has 1–30 carbon atoms, more preferably 2–30 carbon atoms, still more preferably 4–30 carbon atoms, most preferably 6–30 carbon atoms. The alkyl group may be straight or branched, and may have a substituent. Examples of the substituent include a halogen atom, an alkoxy group (methoxy, ethoxy, methoxyethoxy, phenoxy etc.), a sulfide group (methylthio, ethylthio, propylthio etc.), an alkylamino group (methylamino, propylamino etc.), an acyl group (acetyl, propanoyl, octanoyl, benzoyl etc.), an acyloxy group (acetoxy, pivaloyloxy, benzoyloxy etc.), a hydroxyl, a mercapto, an amino, a carboxyl, a sulfo, a carbamoyl, a sulfamoyl, a ureido and so forth.

Preferred ranges of carbon numbers of the alkenyl group and alkynyl group represented by $R^1$ are the same as that of the aforementioned alkyl group, and the alkenyl group and alkynyl group may be straight or branched. Furthermore, the alkenyl group and alkynyl group represented by $R^1$ may have a substituent, and examples of the substituent are similar to those exemplified as substituents of the aforementioned alkyl group.

Examples of the aryl group represented by $R^1$ include phenyl group, indenyl group, a-naphthyl group, β-naphthyl group, fluorenyl group, phenanthrenyl group, anthracenyl group, pyrenyl group and so forth, and phenyl group and naphthyl group are preferred. Further, the aryl group may have a substituent, and examples of the substituent include an alkyl group, beside those exemplified as substituents of the aforementioned alkyl group. The aforementioned substituent is preferably a straight or branched alkyl group having 8 or more carbon atoms or a substituent containing an alkyl residue of such an alkyl group, and specifically, preferred are substituents of an alkyl group (octyl, decyl, hexadecyl, 2-ethylhexyl, etc.), an alkoxy group (dodecyloxy, hexadecyloxy etc.), a sulfide group (hexadecylthio etc.), a substituted amino group (heptadecylamino), octylcarbamoyl, octanoyl, decylsulfamoyl and so forth. Further, the aryl group preferably has two or more of these substituents, and it may be substituted with, besides the substituents mentioned above, a halogen atom, a hydroxy, a cyano, a nitro, a carboxyl, a sulfo or the like.

Like the heterocyclic group represented by D, the heterocyclic group represented by $R^1$ preferably has a 5- to 7-membered ring, more preferably a 5-membered or 6-membered ring. Specific examples of such a basic structure include those mentioned in Iwanami Dictionary of Physics and Chemistry (Iwanami Rikagaku Jiten), 3rd Supplemented Edition, published by Iwanami Shoten, Appendix, Chapter 11, Nomenclature of Organic Chemistry, Table 4: Designations of Major Heterocyclic Monocyclic Compounds, p. 1606 and Table 5: Designations of Major Condensed Heterocyclic Compounds, p. 1607. These heterocyclic groups may have a substituent like the aryl group, and the substituent is preferably a substituent containing a straight or branched alkyl residue having 8 or more carbon atoms. Further, the heterocyclic group preferably has two or more of these substituents, and it is preferably substituted with, for example, besides the substituents mentioned above, a halogen atom, a hydroxy, a cyano, a nitro, a carboxyl, a sulfo or the like.

In the aforementioned formula (1), $R^2$ represents a halogen atom, a hydroxy, an unsubstituted amino, a mercapto, a cyano, a sulfide, a carboxy or salt thereof, a sulfo or salt thereof, a hydroxyamino, a ureido or a urethane. Among these, $R^2$ preferably represents a halogen atom, a hydroxy, an unsubstituted amino or a mercapto, more preferably a halogen atom.

In the aforementioned formula (1), m represents 1 or 2, and n represents an integer of 1 or larger. When m and n are 2 or larger, 2 or more of X, $R^1$ and $R^2$ may be identical to or different from each other or one another, respectively. m is preferably 2.

Among the heterocyclic ring-containing compounds represented by the aforementioned formula (1), heterocyclic ring-containing compounds represented by the following formula (2) are preferred.

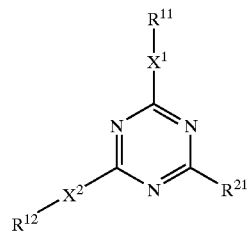

Formula (2)

In the aforementioned formula (2), $X^1$ and $X^2$ each independently represent a divalent linking group consisting of a single bond, $NR^3$ group, an oxygen atom, a sulfur atom, a carbonyl, a sulfonyl or a combination thereof, and $R^3$ represents a hydrogen atom or an alkyl group having 1–30 carbon atoms (including straight and branched alkyl groups). Examples of the divalent linking group consisting of a combination of the groups include oxycarbonyl, aminocarbonyl, carbamoyl, oxysulfonyl, sulfamoyl and so forth. When $X^1$ and $X^2$ each represent a single bond, the triazine ring is directly substituted with each of $R^1$ and $R^{12}$. If $X^1$ and $X^2$ each represent a single bond and $R^{11}$ and $R^{12}$ each represent a heterocyclic group, a heterocyclic group such as piperidine may directly bond at a nitrogen atom having a free valence, or the heterocyclic residue may bond even at a hetero atom that does not have a free valence to form an onium salt such as oxonium salt, sulfonium salt and ammonium salt. $X^1$ and $X^2$ each preferably represent a sulfur atom or $NR^3$ group, and $R^3$ is preferably an alkyl group having 3 or less carbon atoms or a hydrogen atom.

In the aforementioned formula (2), $R^{11}$ and $R^{12}$ each independently represent an alkyl group, an alkenyl group, an alkynyl group, an aryl group or a heterocyclic group, which may be substituted or unsubstituted.

The alkyl group represented by $R^{11}$ and $R^{12}$ preferably has 1–30 carbon atoms, more preferably 2–30 carbon atoms, still more preferably 4–30 carbon atoms, most preferably 6–30 carbon atoms. The alkyl group may be straight or branched, and may have a substituent. Examples of the substituent include a halogen atom, an alkoxy group (methoxy, ethoxy, methoxyethoxy, phenoxy etc.), a sulfide group (methylthio, ethylthio, propylthio etc.), an alkylamino group (methylamino, propylamino etc.), an acyl group (acetyl, propanoyl, octanoyl, benzoyl etc.), an acyloxy group (acetoxy, pivaloyloxy, benzoyloxy etc.), a hydroxyl, a mercapto, an amino, a carboxyl, a sulfo, a carbamoyl, a sulfamoyl, a ureido and so forth.

Preferred ranges of carbon numbers of the alkenyl group and alkynyl group represented by $R^{11}$ or $R^{12}$ are the same as that of the aforementioned alkyl group, and the alkenyl group and alkynyl group may be straight or branched. Furthermore, the alkenyl group and alkynyl group represented by $R^{11}$ or $R^{12}$ may have a substituent, and examples of the substituent are similar to those exemplified as substituents of the aforementioned alkyl group.

Examples of the aryl group represented by $R^{11}$ or $R^{12}$ include phenyl group, indenyl group, a-naphthyl group, β-naphthyl group, fluorenyl group, phenanthrenyl group, anthracenyl group, pyrenyl group and so forth, and phenyl group and naphthyl group are preferred. Further, the aryl group may have a substituent, and examples of the substituent include an alkyl group, beside those exemplified as substituents of the aforementioned alkyl group. The aforementioned substituent is preferably a straight or branched alkyl group having 8 or more carbon atoms or a substituent containing an alkyl residue of such an alkyl group, and specifically, preferred are substituents of an alkyl group (octyl, decyl, hexadecyl, 2-ethylhexyl, etc.), an alkoxy group (dodecyloxy, hexadecyloxy etc.), a sulfide group (hexadecylthio etc.), a substituted amino group (heptadecylamino etc.), octylcarbamoyl, octanoyl, decylsulfamoyl and so forth. Further, the aryl group preferably has two or more of these substituents, and it may be substituted with, besides the substituents mentioned above, a halogen atom, a hydroxy group, a cyano group, a nitro group, a carboxyl group, a sulfo group or the like.

Like the heterocyclic group represented by D, the heterocyclic group represented by $R^{11}$ or $R^{12}$ is preferably a 5- to 7-membered ring residue, more preferably a 5-membered or 6-membered ring residue. Specific examples of such a basic structure include those mentioned in Iwanami Dictionary of Physics and Chemistry (Iwanami Rikagaku Jiten), 3rd Supplemented Edition, published by Iwanami Shoten, Appendix, Chapter 11, Nomenclature of Organic Chemistry, Table 4: Designations of Major Heterocyclic Monocyclic Compounds, p. 1606 and Table 5: Designations of Major Condensed Heterocyclic Compounds, p. 1607. These heterocyclic groups may have a substituent like the aryl group, and the substituent is preferably a substituent containing a straight or branched alkyl residue having 8 or more carbon atoms. Further, the heterocyclic group preferably has two or more of these substituents, and it may be substituted with, besides the substituents mentioned above, a halogen atom, a hydroxy, a cyano, a nitro, a carboxyl, a sulfo or the like.

$R^1$ and $R^{12}$ more preferably contains a straight or branched alkyl chain having 8 or more carbon atoms in total, a straight or branched oligoalkyleneoxy chain having 4 or more carbon atoms in total, a straight or branched perfluoroalkyl chain having 2 or more carbon atoms in total, a straight or branched perfluoroalkyl ether chain having 2 or more carbon atoms in total or a straight or branched organic polysilyl chain. $R^{11}$ and $R^{12}$ particularly preferably represent a phenyl group substituted with a substituent containing a straight or branched alkyl residue having 8 or more carbon atoms.

In the aforementioned formula (2), $R^{21}$ represents a halogen atom, a hydroxy, an unsubstituted amino, a mercapto, a cyano, a sulfide, a carboxy or salt thereof, a sulfo or salt thereof, a hydroxyamino, a ureido or a urethane. Among these, $R^{21}$ preferably represents a halogen atom, a hydroxy group, an unsubstituted amino group or a mercapto group, more preferably a halogen atom.

Preferred embodiments of the heterocyclic ring-containing compounds represented by the aforementioned formula (2) are the heterocyclic ring-containing compounds, wherein $X^1$ and $X^2$ represent a sulfur atom or an imino group (—NH—) (more preferably an imino group); and/or the heterocyclic ring-containing compounds, wherein $R^{21}$ represents a halogen atoms. And another preferred embodiment of the heterocyclic ring-containing compound represented by the aforementioned formula (2) is the heterocyclic ring-containing compound, wherein at least one of $R^{11}$ and $R^{12}$ contains —(C═O)O—.

Furthermore, the compounds represented by the following formula (3) can be mentioned as preferred embodiments of the compounds represented by the aforementioned formula (2), the compounds represented by the following formula (4) can be mentioned as more preferred embodiments of the compounds represented by the aforementioned formula (2); the compounds represented by the following formula (5) can be mentioned as still more preferred embodiments of the compounds represented by the aforementioned formula (2).

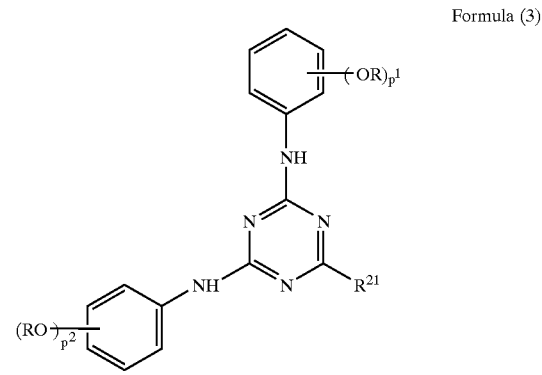

Formula (3)

In the aforementioned formula (3), R represents an alkyl group having 8 or more carbon atoms, an oligoalkyleneoxy group having 4 or more carbon atoms or a perfluoroalkyl group having 2 or more carbon atoms, and $p^1$ and $p^2$ each independently represent 1 or 2. $R^{21}$ has the same meaning as defined in the aforementioned formula (2), and the preferred range thereof is also similar to that of $R^{21}$ mentioned in the aforementioned formula (2). That is, $R^{21}$ preferably represents a halogen atom, a hydroxy, an unsubstituted amino or a mercapto, more preferably a halogen atom.

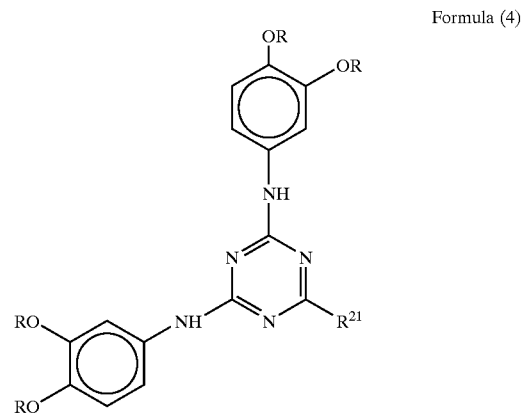

Formula (4)

In the aforementioned formula (4), R represents an alkyl group having 8 or more carbon atoms, an oligoalkyleneoxy group having 4 or more carbon atoms or a perfluoroalkyl group having 2 or more carbon atoms. $R^{21}$ has the same meaning as defined in the aforementioned formula (2), and the preferred range thereof is also similar to that of $R^{21}$ mentioned in the aforementioned formula (2). That is, $R^{21}$ preferably represents a halogen atom, a hydroxy, an unsubstituted amino or a mercapto, more preferably a halogen atom.

Formula (5)

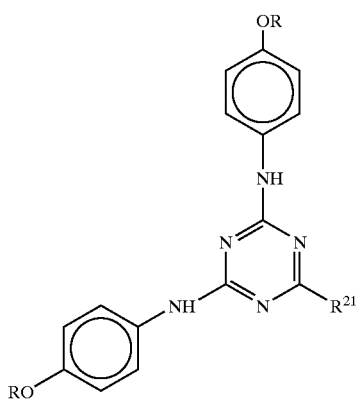

Formula (7)

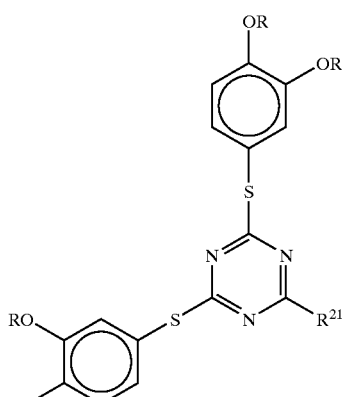

In the aforementioned formula (5), R represents an alkyl group having 8 or more carbon atoms, an oligoalkyleneoxy group having 4 or more carbon atoms or a perfluoroalkyl group having 2 or more carbon atoms. $R^{21}$ has the same meaning as defined in the aforementioned formula (2), and the preferred range thereof is also similar to that of $R^{21}$ mentioned in the aforementioned formula (2). That is, $R^{21}$ preferably represents a halogen atom, a hydroxy, an unsubstituted amino or a mercapto, more preferably a halogen atom.

As another embodiments of the present invention, there are provided compounds represented by the following formulas (6) to (8).

Formula (6)

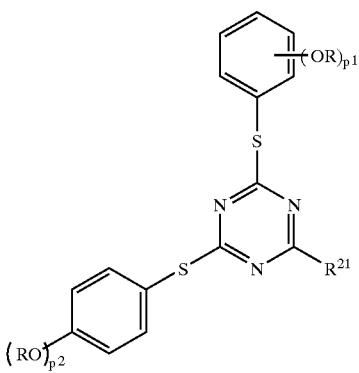

Formula (8)

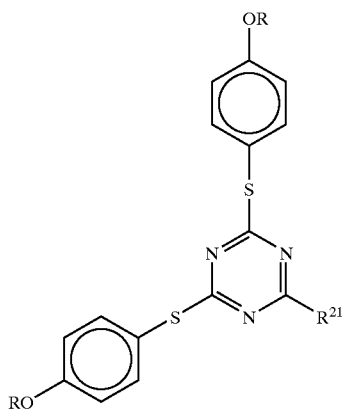

In the formulas (6) to (8), R, $R^{21}$, $p^1$ and $p^2$ each have the same meanings as defined in the aforementioned formula (3).

In the aforementioned formulas (3) to (8), at least one of R preferably contains —(C=O)O—.

Specific examples of the compounds represented by the aforementioned formula (1) will be mentioned below. However, the present invention is not limited to the following specific examples.

| | D | X | $R^1$ | m | $R^2$ | n |
|---|---|---|---|---|---|---|
| T-1 | triazine | —NH— | O(CH₂CH₂O)₂—C₆H₁₃, o-tolyl | 2 | —NH₂ | 1 |

| | D | X | R¹ | m | R² | n |
|---|---|---|---|---|---|---|
| T-2 | triazine | —S— | 4-methylphenyl with 2-OCH₂CH(C₆H₁₃)C₈H₁₇ and 3-OCH₂CH(C₈H₁₇)C₆H₁₃ | 2 | —NH₂ | 1 |
| T-3 | triazine | —NH— | 4-methylphenyl with 2-O(CH₂CH₂O)₂—C₆H₁₃ and 3-O(CH₂CH₂O)₂—C₆H₁₃ | 2 | —OH | 1 |
| T-4 | triazine | —NH— | 4-methylphenyl with 2-O(CH₂CH₂CCHMeCH₂)₄H and 3-O(CH₂CH₂CCHMeCH₂)₄H | 2 | —SH | 1 |
| T-5 | triazine | —S— | 4-methylphenyl with 2-OC₁₆H₃₃ and 3-OC₁₆H₃₃ | 2 | —NHOH | 1 |
| X-1 | triazine | —NHSO₂— | 2-[O(CH₂CH₂O)₂—C₆H₁₃]phenyl | 2 | —Cl | 1 |
| X-2 | triazine | —NHSO₂NH— | 4-methylphenyl with 2-OCH₂CH(C₆H₁₃)C₈H₁₇ and 3-OCH₂CH(C₈H₁₇)C₆H₁₃ | 2 | —Cl | 1 |
| X-3 | triazine | —NHCONH— | 4-methylphenyl with 2-O(CH₂CH₂O)₂—C₆H₁₃ and 3-O(CH₂CH₂O)₂—C₆H₁₃ | 2 | —Cl | 1 |
| X-4 | triazine | —O— | 4-methylphenyl with 2-O(CH₂CH₂CCHMeCH₂)₄H and 3-O(CH₂CH₂CCHMeCH₂)₄H | 2 | —Cl | 1 |
| X-5 | triazine | —N(CH₃)— | 4-methylphenyl with 2-OC₁₆H₃₃ and 3-OC₁₆H₃₃ | 2 | —Cl | 1 |

-continued

| | D | X | R¹ | m | R² | n |
|---|---|---|---|---|---|---|
| N-1 | triazine | —NH— | —C₆H₄—OC₁₂H₂₅ (para) | 2 | —Cl | 1 |
| N-2 | triazine | —NH— | —C₆H₄—OCH₂CH(C₆H₁₃)—C₈H₁₇ (para) | 2 | —Cl | 1 |
| N-3 | triazine | —NH— | —C₆H₄—O(CH₂CH₂O)₂—C₆H₁₃ (para) | 2 | —Cl | 1 |
| N-4 | triazine | —NH— | —C₆H₄—O(CH₂CH₂CCHMeCH₂)₄H (para) | 2 | —Cl | 1 |
| N-5 | triazine | —NH— | —C₆H₄—O(CH₂CH₂O)₂C₆H₁₃ (meta) | 2 | —Cl | 1 |
| N-6 | triazine | —NH— | —C₆H₄—O(CH₂CH₂O)₂—C₆H₁₃ (ortho) | 2 | —Cl | 1 |
| N-7 | triazine | —NH— | —C₆H₃[OCH₂CH(C₆H₁₃)C₈H₁₇][OCH₂CH(C₆H₁₃)C₈H₁₇] | 2 | —Cl | 1 |
| N-8 | triazine | —NH— | —C₆H₃[O(CH₂CH₂O)₂—C₆H₁₃][O(CH₂CH₂O)₂—C₆H₁₃] | 2 | —Cl | 1 |
| N-9 | triazine | —NH— | —C₆H₃[O(CH₂CH₂CCHMeCH₂)₄H][O(CH₂CH₂CCHMeCH₂)₄H] | 2 | —Cl | 1 |

-continued
| | D | X | R¹ | m | R² | n |
|---|---|---|---|---|---|---|
| N-10 |  | —N(H)— |  | 2 | —Cl | 1 |
| N-11 |  | —N(H)— |  | 2 | —Cl | 1 |
| N-12 |  | —N(H)— |  | 2 | —Cl | 1 |
| N-13 |  | —N(H)— |  | 2 | —Cl | 1 |
| N-14 |  | —N(H)— |  | 2 | —Cl | 1 |
| N-15 |  | —N(H)— |  | 2 | —Cl | 1 |
| N-16 |  | —N(H)— | —C$_{16}$H$_{33}$ | 2 | —Cl | 1 |
| N-17 |  | —N(H)— |  | 2 | —Cl | 1 |
| N-18 |  | —N(H)— | —(CH$_2$)$_3$OC$_{18}$H$_{37}$ | 2 | —Cl | 1 |
| N-19 |  | —N(H)— |  | 2 | —Cl | 1 |

-continued

| | D | X | R¹ | m | R² | n |
|---|---|---|---|---|---|---|
| N-20 | triazine (2,4,6-trimethyl-1,3,5-triazine) | | N-methylisoindole with 5,6-bis(O(CH$_2$CH$_2$O)$_2$—C$_6$H$_{13}$) | 2 | —Cl | 1 |
| N-21 | triazine | —NH— | phenyl with O—(CH$_2$)$_{10}$CO$_2$CH$_3$ (×2) | 2 | —Cl | 1 |
| N-22 | triazine | —NH— | phenyl with O—(CH$_2$)$_{10}$CO$_2$C$_8$H$_{17}$ (×2) | 2 | —Cl | 1 |
| N-23 | triazine | —NH— | phenyl with O—(CH$_2$)$_{10}$CO$_2$C$_{12}$H$_{25}$ (×2) | 2 | —Cl | 1 |
| N-24 | triazine | —NH— | phenyl with O—(CH$_2$)$_{10}$CO$_2$CH$_2$CH$_2$C$_8$F$_{17}$ (×2) | 2 | —Cl | 1 |
| N-25 | triazine | —NH— | phenyl with O—(CH$_2$)$_{10}$CO$_2$—CH$_2$—CH(C$_2$H$_5$)—C$_4$H$_9$ (×2) | 2 | —Cl | 1 |
| N-26 | triazine | —NH— | phenyl with O—(CH$_2$)$_4$CO$_2$—(CH$_2$CH$_2$O)$_2$C$_6$H$_{13}$ (×2) | 2 | —Cl | 1 |
| N-27 | triazine | —NH— | phenyl with O—(CH$_2$)$_7$CO$_2$—(CH$_2$CH$_2$O)$_2$C$_6$H$_{13}$ (×2) | 2 | —Cl | 1 |
| N-28 | triazine | —NH— | phenyl with O—(CH$_2$)$_{10}$CO$_2$—(CH$_2$CH$_2$O)$_2$C$_6$H$_{13}$ (×2) | 2 | —Cl | 1 |

-continued

| | D | X | R¹ | m | R² | n |
|---|---|---|---|---|---|---|
| N-29 | triazine | —NH— | 2,4-disubstituted phenyl with both O—(CH$_2$)$_{10}$CO$_2$—(CH$_2$CH$_2$O)$_3$CH$_3$ | 2 | —Cl | 1 |
| N-30 | triazine | —NH— | 2,4-disubstituted phenyl with both O—(CH$_2$)$_{10}$CO$_2$—(CH$_2$CH$_2$O)$_4$C$_{12}$H$_{25}$ | 2 | —Cl | 1 |
| N-31 | triazine | —NH— | -C$_6$H$_4$-O—(CH$_2$)$_{10}$CO$_2$CH$_3$ | 2 | —Cl | 1 |
| N-32 | triazine | —NH— | -C$_6$H$_4$-O—(CH$_2$)$_{10}$CO$_2$C$_{12}$H$_{25}$ | 2 | —Cl | 1 |
| N-33 | triazine | —NH— | -C$_6$H$_4$-O—(CH$_2$)$_{10}$CO$_2$—CH$_2$—CH(C$_2$H$_5$)—C$_4$H$_9$ | 2 | —Cl | 1 |
| N-34 | triazine | —NH— | -C$_6$H$_4$-O—(CH$_2$)$_{10}$CO$_2$—(CH$_2$CH$_2$O)$_2$C$_6$H$_{13}$ | 2 | —Cl | 1 |
| N-35 | triazine | —NH— | -C$_6$H$_4$-O—(CH$_2$)$_{10}$CO$_2$—(CH$_2$CH$_2$O)$_3$CH$_3$ | 2 | —Cl | 1 |
| S-1 | triazine | —S— | -C$_6$H$_4$-OC$_{12}$H$_{25}$ | 2 | —Cl | 1 |
| S-2 | triazine | —S— | -C$_6$H$_4$-OCH$_2$CH(C$_6$H$_{13}$)—C$_8$H$_{17}$ | 2 | —Cl | 1 |
| S-3 | triazine | —S— | -C$_6$H$_4$-O(CH$_2$CH$_2$O)$_2$—C$_6$H$_{13}$ | 2 | —Cl | 1 |

-continued
| | D | X | R¹ | m | R² | n |
|---|---|---|---|---|---|---|
| S-4 | 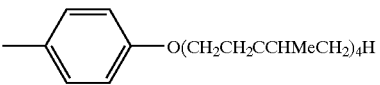 | —S— | 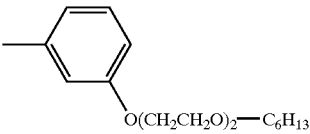 —O(CH₂CH₂CCHMeCH₂)₄H | 2 | —Cl | 1 |
| S-5 | 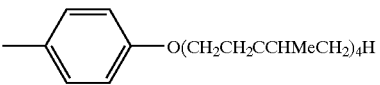 | —S— | 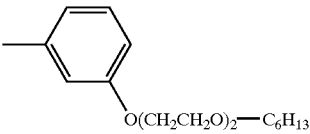 O(CH₂CH₂O)₂—C₆H₁₃ | 2 | —Cl | 1 |
| S-6 | 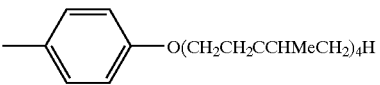 | —S— | 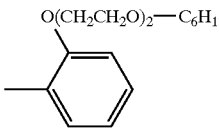 O(CH₂CH₂O)₂—C₆H₁₃ | 2 | —Cl | 1 |
| S-7 | 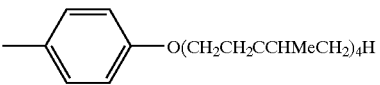 | —S— | 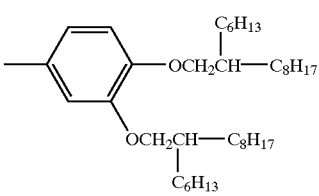 OCH₂CH(C₆H₁₃)—C₈H₁₇ / OCH₂CH(C₆H₁₃)—C₈H₁₇ | 2 | —Cl | 1 |
| S-8 | 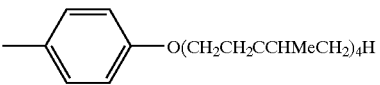 | —S— | 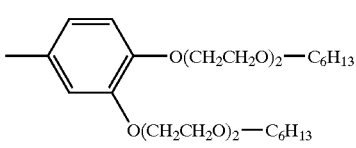 O(CH₂CH₂O)₂—C₆H₁₃ / O(CH₂CH₂O)₂—C₆H₁₃ | 2 | —Cl | 1 |
| S-9 | 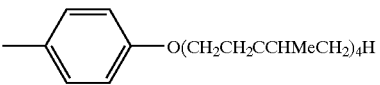 | —S— | 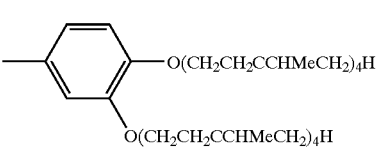 O(CH₂CH₂CCHMeCH₂)₄H / O(CH₂CH₂CCHMeCH₂)₄H | 2 | —Cl | 1 |
| S-10 | 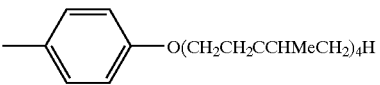 | —S— | 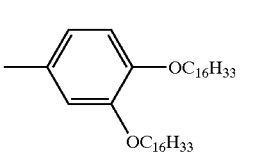 OC₁₆H₃₃ / OC₁₆H₃₃ | 2 | —Cl | 1 |
| S-11 | 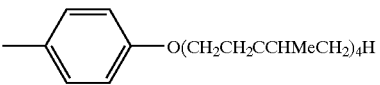 | —S— | 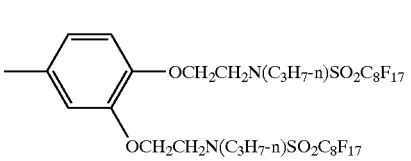 OCH₂CH₂N(C₃H₇-n)SO₂C₈F₁₇ / OCH₂CH₂N(C₃H₇-n)SO₂C₈F₁₇ | 2 | —Cl | 1 |
| S-12 | 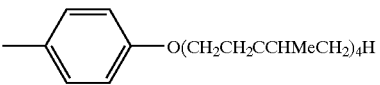 | —S— | 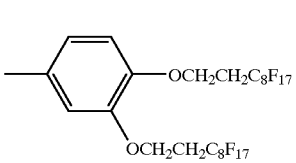 OCH₂CH₂C₈F₁₇ / OCH₂CH₂C₈F₁₇ | 2 | —Cl | 1 |

-continued

| | D | X | R¹ | m | R² | n |
|---|---|---|---|---|---|---|
| S-13 | triazine | —S— | phenyl with —O(C=O)(CF$_2$)$_6$CF$_3$ and —O(C=O)(CF$_2$)$_6$CF$_3$ | 2 | —Cl | 1 |
| S-14 | triazine | —S— | phenyl with —OCH$_2$(C=O)OC$_{10}$H$_{21}$ and —OCH$_2$(C=O)OC$_{10}$H$_{21}$ | 2 | —Cl | 1 |
| S-15 | triazine | —S— | phenyl with —O(SiMe$_2$O)$_6$(C$_2$H$_4$)$_4$OCH$_3$ and —O(SiMe$_2$O)$_6$(C$_2$H$_4$)$_4$OCH$_3$ | 2 | —Cl | 1 |
| S-16 | triazine | —S— | —C$_{16}$H$_{33}$ | 2 | —Cl | 1 |
| S-17 | triazine | —S— | —H$_2$C—phenyl with —O(CH$_2$CH$_2$O)$_2$—C$_6$H$_{13}$ and —O(CH$_2$CH$_2$O)$_2$—C$_6$H$_{13}$ | 2 | —Cl | 1 |
| S-18 | triazine | —S— | —(CH$_2$)$_3$OC$_{18}$H$_{37}$ | 2 | —Cl | 1 |
| S-19 | triazine | —S— | 2-methylbenzothiazole with —OC$_{16}$H$_{33}$ and —OC$_{16}$H$_{33}$ | 2 | —Cl | 1 |
| S-20 | triazine | —S— | phenyl with —O—(CH$_2$)$_{10}$CO$_2$CH$_3$ and —O—(CH$_2$)$_{10}$CO$_2$CH$_3$ | 2 | —Cl | 1 |
| S-21 | triazine | —S— | phenyl with —O—(CH$_2$)$_{10}$CO$_2$C$_2$H$_5$ and —O—(CH$_2$)$_{10}$CO$_2$C$_2$H$_5$ | 2 | —Cl | 1 |
| S-22 | triazine | —S— | phenyl with —O—(CH$_2$)$_{10}$CO$_2$C$_8$H$_{17}$ and —O—(CH$_2$)$_{10}$CO$_2$C$_8$H$_{17}$ | 2 | —Cl | 1 |

-continued

| | D | X | R¹ | m | R² | n |
|---|---|---|---|---|---|---|
| S-23 | triazine | —S— | aryl with O—(CH$_2$)$_{10}$CO$_2$C$_{12}$H$_{25}$ and O—(CH$_2$)$_{10}$CO$_2$C$_{12}$H$_{25}$ | 2 | —Cl | 1 |
| S-24 | triazine | —S— | aryl with O—(CH$_2$)$_{10}$CO$_2$CH$_2$CH$_2$C$_8$F$_{17}$ and O—(CH$_2$)$_{10}$CO$_2$CH$_2$CH$_2$C$_8$F$_{17}$ | 2 | —Cl | 1 |
| S-25 | triazine | —S— | aryl with O—(CH$_2$)$_{10}$CO$_2$—CH$_2$—CH(C$_2$H$_5$)—C$_4$H$_9$ and O—(CH$_2$)$_{10}$CO$_2$—CH$_2$—CH(C$_2$H$_5$)—C$_4$H$_9$ | 2 | —Cl | 1 |
| S-26 | triazine | —S— | aryl with O—(CH$_2$)$_4$CO$_2$—(CH$_2$CH$_2$O)$_2$C$_6$H$_{13}$ and O—(CH$_2$)$_4$CO$_2$—(CH$_2$CH$_2$O)$_2$C$_6$H$_{13}$ | 2 | —Cl | 1 |
| S-27 | triazine | —S— | aryl with O—(CH$_2$)$_7$CO$_2$—(CH$_2$CH$_2$O)$_2$C$_6$H$_{13}$ and O—(CH$_2$)$_7$CO$_2$—(CH$_2$CH$_2$O)$_2$C$_6$H$_{13}$ | 2 | —Cl | 1 |
| S-28 | triazine | —S— | aryl with O—(CH$_2$)$_{10}$CO$_2$—(CH$_2$CH$_2$O)$_2$C$_6$H$_{13}$ and O—(CH$_2$)$_{10}$CO$_2$—(CH$_2$CH$_2$O)$_2$C$_6$H$_{13}$ | 2 | —Cl | 1 |
| S-29 | triazine | —S— | aryl with O—(CH$_2$)$_{10}$CO$_2$—(CH$_2$CH$_2$O)$_3$CH$_3$ and O—(CH$_2$)$_{10}$CO$_2$—(CH$_2$CH$_2$O)$_3$CH$_3$ | 2 | —Cl | 1 |
| S-30 | triazine | —S— | aryl with O—(CH$_2$)$_{10}$CO$_2$—(CH$_2$CH$_2$O)$_4$C$_{12}$H$_{25}$ and O—(CH$_2$)$_{10}$CO$_2$—(CH$_2$CH$_2$O)$_4$C$_{12}$H$_{25}$ | 2 | —Cl | 1 |
| S-31 | triazine | —S— | aryl with O—(CH$_2$)$_{10}$CO$_2$CH$_3$ | 2 | —Cl | 1 |

-continued

| | D | X | R¹ | m | R² | n |
|---|---|---|---|---|---|---|
| S-32 | triazine | —S— | -C₆H₄-O—(CH₂)₁₀CO₂C₁₂H₂₅ | 2 | —Cl | 1 |
| S-33 | triazine | —S— | -C₆H₄-O—(CH₂)₁₀CO₂—CH₂CH(C₂H₅)—C₄H₉ | 2 | —Cl | 1 |
| S-34 | triazine | —S— | -C₆H₄-O—(CH₂)₁₀CO₂—(CH₂CH₂O)₂C₆H₁₃ | 2 | —Cl | 1 |
| S-35 | triazine | —S— | -C₆H₄-O—(CH₂)₁₀CO₂—(CH₂CH₂O)₃CH₃ | 2 | —Cl | 1 |
| P-1 | triazine | —NH— | -C₆H₄-O(CH₂CH₂O)₂—C₆H₁₃ | 2 | NH(C=O)NH₂ | 1 |
| P-2 | triazine | —NH— | -C₆H₃(-OCH₂CH(C₆H₁₃)—C₈H₁₇)(-OCH₂CH(C₆H₁₃)—C₈H₁₇) | 2 | —CN | 1 |
| P-3 | triazine | —NH— | -C₆H₃(-O(CH₂CH₂O)₂—C₆H₁₃)(-O(CH₂CH₂O)₂—C₆H₁₃) | 2 | —COOH | 1 |
| P-4 | triazine | —S— | -C₆H₃(-O(CH₂CH₂CCHMeCH₂)₄H)(-O(CH₂CH₂CCHMeCH₂)₄H) | 2 | —SO₃H | 1 |
| P-5 | triazine | —S— | -C₆H₃(-OC₁₆H₃₃)(-OC₁₆H₃₃) | 2 | —COOH | 1 |

| | D | X | R¹ | m | R² | n |
|---|---|---|---|---|---|---|
| P-6 | triazine | —NH— | 2-methylphenyl with O(CH₂CH₂O)₂—C₆H₁₃ | 2 | SCH3 | 1 |
| P-7 | triazine | —NH— | phenyl with OCH₂CH(C₆H₁₃)—C₈H₁₇ and OCH₂CH(C₆H₁₃)—C₈H₁₇ | 2 | —COONa | 1 |
| P-8 | triazine | —S— | phenyl with O(CH₂CH₂O)₂—C₆H₁₃ and O(CH₂CH₂O)₂—C₆H₁₃ | 2 | —SO₃Na | 1 |
| P-9 | triazine | —S— | phenyl with O(CH₂CH₂CCHMeCH₂)₄H and O(CH₂CH₂CCHMeCH₂)₄H | 2 | —NHCOOCH₃ | 1 |
| P-10 | triazine | —S— | phenyl—O—(CH₂)₁₀CO₂—(CH₂CH₂O)₂C₆H₁₃ | 2 | —I | 1 |
| P-11 | triazine | —S— | phenyl—O—(CH₂)₁₀CO₂C₁₂H₂₅ | 2 | —I | 1 |
| P-12 | triazine | —NH— | phenyl—O—(CH₂)₁₀CO₂—CH₂—CH(C₂H₅)—C₄H₉ | 2 | —I | 1 |
| P-13 | triazine | —NH— | phenyl—O—(CH₂)₁₀CO₂—(CH₂CH₂O)₂C₆H₁₃ | 2 | —I | 1 |
| P-14- | triazine | —NH— | phenyl—O—(CH₂)₁₀CO₂—(CH₂CH₂O)₃CH₃ | 2 | —I | 1 |

-continued

| D | X | R¹ | m | R² | n |
|---|---|---|---|---|---|

H-1: D = pyrimidine (C, B positions with N); A,B = —NH—C₆H₃(O(CH₂CH₂O)₂—C₆H₁₃)(O(CH₂CH₂O)₂—C₆H₁₃); C = NH₂

H-2: D = pyrimidine; B,C = —S—C₆H₄—O(CH₂CH₂CCHMeCH₂)₄H; A = SH

The heterocyclic ring-containing compounds of the present invention can be produced, for example, according to Synthesis Examples 1 and 2 mentioned below. $X^1$, $R^{11}$, $R^{21}$ and $p^1$ in the formulas have the same meanings as defined in the aforementioned formulas (1) to (3). R' in the formulas represents a substituent, which is represented by, for example, —OR in the aforementioned formula (3).

Synthesis Example 1

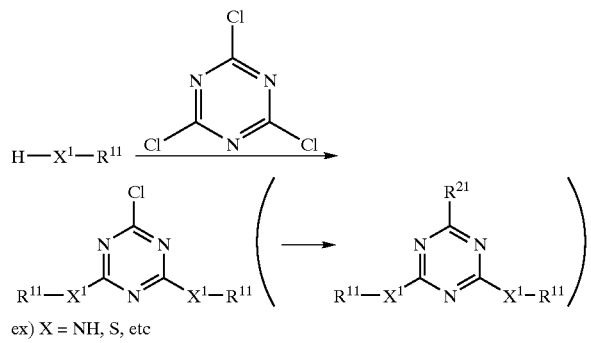

ex) X = NH, S, etc

Synthesis Example 2

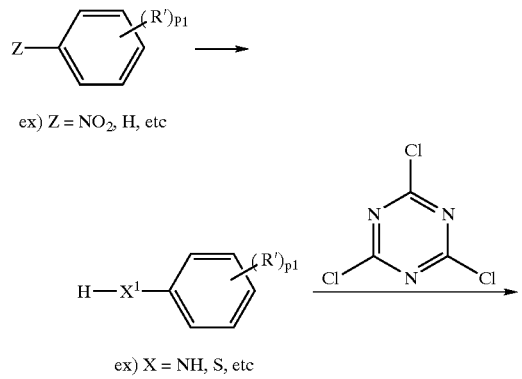

ex) Z = NO₂, H, etc

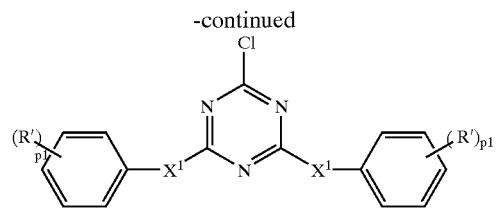

ex) X = NH, S, etc

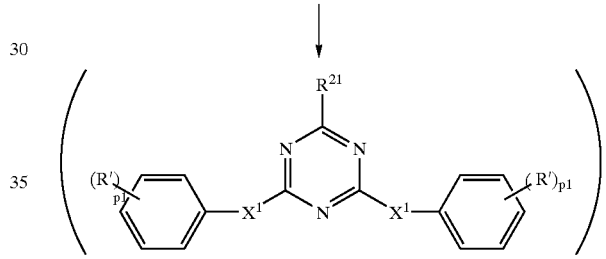

The heterocyclic ring-containing compounds represented by the aforementioned formula (1) alone can be used as a lubricant. Further, the compounds represented by the aforementioned formula (1) can also be used as a lubricating aid in an embodiment in which they are mixed with lubricant base oil. The aforementioned lubricant base oil is not particularly limited, and any of lubricant base oils generally used can be used. Examples thereof include mineral oils, synthetic oils and or mixed oils thereof. There can be mentioned, for example, solvent-refined raffinates obtained by treating a lubricating oil raw material derived from paraffin type, intermediate base type or naphthene type crude oil by ordinary pressure or vacuum distillation with an aromatic extraction solvent such as phenol, furfural and N-methylpyrolidone; hydrogenated oils obtained by bringing a lubricant oil raw material into contact with hydrogen under a hydrogenation treatment condition in the presence of a catalyst for hydrogenation treatment such as cobalt or molybdenum on a carrier of silica-alumina; isomerized oils obtained by bringing a lubricant oil raw material into contact with hydrogen under an isomerization condition of a severe cracking condition in the presence of a hydro-cracking catalyst; lubricating oil fractions obtained from a lubricating oil raw material by a combination of solvent refining process and hydrogenation process, hydro-cracking process and isomerization process or the like, and so forth. In particular, mineral oil showing high viscosity index obtained by hydro-cracking process and isomerization process can be mentioned as a preferred material. In any of the production methods, dewaxing process, finishing process by hydrogenation, clay treatment process and so forth may be arbitrarily performed as an additional process. The aforementioned mineral oils can also be classified into light neutral oil, intermediate neutral oil, heavy neutral oil, bright stock and so forth, and they can also be suitably mixed according to required performances.

Examples of the aforementioned synthetic oils include poly(a-olefin), a-olefin oligomer, polybutene, alkylbenzene, polyol ester, dibasic acid ester, polyoxyalkylene glycol, polyoxyalkylene glycol ether, silicone oil and so forth. These mineral oils and synthetic oils may be used each alone or in any combination of two or more kinds of them, and a mineral oil and a synthetic oil may be used in combination. Such a lubricant base oil usually shows a kinematic viscosity of 2–20 mm$^2$/s, preferably a kinematic viscosity of 3–15 mm$^2$/s, at a temperature of 100° C. There can be arbitrarily selected a mixed base oil showing an optimum kinematic viscosity suitable for lubricating conditions of surfaces sliding with mechanical friction where the lubricant composition of the present invention is used.

When the compounds represented by the aforementioned formula (1) are used as a lubricant by mixing them with the aforementioned lubricant base oil, the aforementioned compounds are preferably mixed in an amount of 0.01 weight % or more, more preferably 0.01–10 weight %, most preferably 0.05–2 weight %, of the total weight of the lubricant base oil. The content of the lubricant base oil is preferably more than 50 weight %. In an embodiment where the lubricant base oil is not contained, the aforementioned compounds are preferably contained in an amount of more than 50 weight %.

Lubricants containing the compounds represented by the aforementioned formula (1) can be used for various purposes. In order to secure performances for practical use suitable for various uses, the lubricants may further be added with various additives used for conventional lubricants such as bearing oil, gear oil and power transmission oil, specifically, anti-wearing agent, extreme-pressure agent, antioxidant, viscosity index improver, detergent-dispersant, metal deactivator, anticorrosive, rust preventive, antifoaming agent and so forth, as required, within such an amount that the effect of the present invention should not be degraded.

The aforementioned lubricant composition exhibits, when it is supplied on surfaces sliding in contact as relative motions, an effect of reducing frictional coefficient of the sliding surfaces and simultaneously improving wear-resistance of the sliding surfaces. Furthermore, it also has an outstanding effect of maintaining the effect for a long period of time. Even if the lubricant composition is supplied on sliding surfaces moving under such a severe friction condition that oil film should be broken even with supply of a conventional lubricant such as lubricating oil or grease, it can reduce seizing, improve wear resistance and maintain a low friction coefficient. It can be suitably used as an energy-saving type lubricant for, for example, bearings and gears, which move under a severe friction condition. Furthermore, it can improve reliability of apparatuses including sliding members and can contribute to miniaturization of apparatuses including sliding members. Further, the aforementioned lubricant composition is also characterized by showing a low friction coefficient, superior abrasion resistance, extreme pressure property and so forth under a severe lubricating condition. As for these properties, one can refer to the descriptions of Japanese Patent Laid-open Publication Nos. 6-16968, 8-319494, 9-328694, 10-183154, 10-298581, 10-147790, 10-330778, 2000-154391, WO98/22472, Japanese Patent Laid-open Publication No. 2000-355695 and so forth.

Since the compounds represented by the aforementioned formula (1) show superior lubricating effect by themselves, they can be preferably used for apparatuses that cannot be supplied with a lot of lubricant, for example, micromachines. Further, since the compounds represented by the aforementioned formula (1) have a property of readily form a coating film on a surface of metal, metal oxide and so forth and exhibiting the lubricating function, they are also preferably used as a lubricant for reducing friction between a surface of magnetic recording medium and a magnetic recording head.

The heterocyclic ring-containing compounds of the present invention can be used as, besides a lubricant or lubricating aid, a surface treating agent for metal base materials, for example, a metal surface treating agent that can reduce surface energy of metal surface by a treatment with it and thereby control adhesion or improve wetting property, water-repellency, antifouling property, rust proof property, mold-release property and so forth. Further, they can also be used as a liquid crystal orientation controlling agent for controlling orientation of liquid crystal and an ice-coating inhibitor that prevents ice coating on windowpanes of automobiles.

EXAMPLES

The present invention will be more specifically explained with reference to the following examples. Materials, reagents, proportions, procedures and so forth mentioned in the following examples can be appropriately changed unless such changes depart from the spirit of the present invention. Accordingly, the scope of the present invention is not limited to the following specific examples.

[Synthesis Example for N-8]

Compound N-8 was synthesized according to the following synthetic scheme.

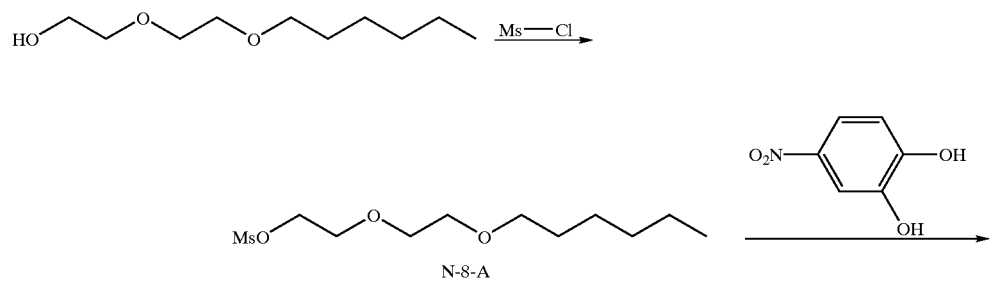

-continued

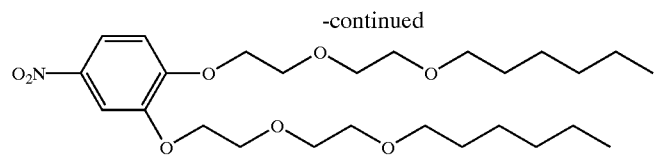

N-8-B

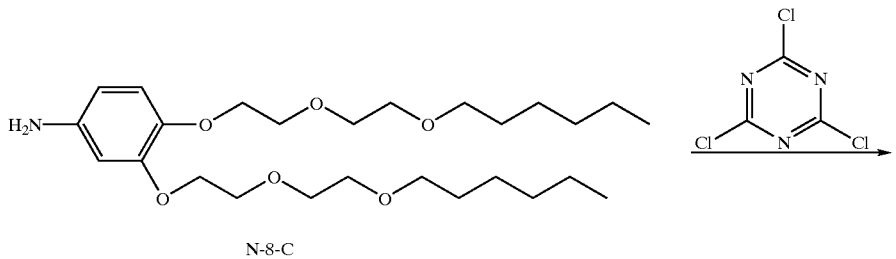

N-8-C

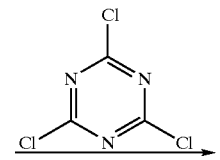

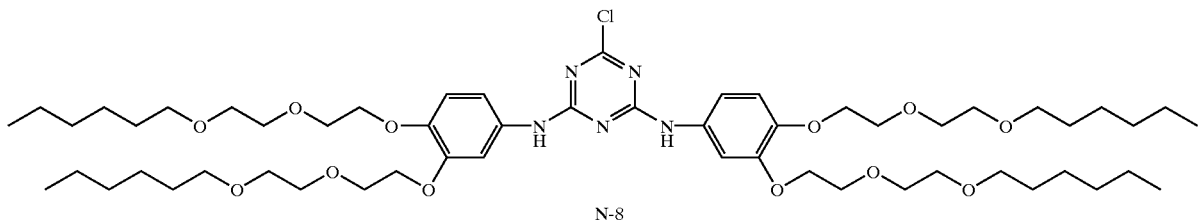

N-8

(Synthesis of Compound (N-8-A))

To a 500-mL three-neck flask provided with a stirrer, 95.1 g (0.5 mol) of diethylene glycol monohexyl ether, 150 mL of tetrahydrofuran and 76.7 mL (0.55 mol) of triethylamine were added and stirred to obtain a solution. The solution was cooled to −5° C., and added dropwise with 38.7 mL (0.5 mol) of methanesulfonyl chloride with stirring the solution. After completion of the addition, the reaction mixture was stirred at room temperature for 2 hours. The reaction mixture was extracted with ethyl acetate and washed with water. Then, the organic layer was separated and dried over anhydrous magnesium sulfate. The solvent was evaporated under reduced pressure to obtain 133.8 g (99.7%) of Compound (N-8-A).

(Synthesis of Compound (N-8-B))

To a 2-L three-neck flask provided with a stirrer, 25 g (0.161 mol) of 4-nitrocatechol, 95.1 g (0.354 mol) of the obtained Compound (N-8-A) and 600 mL of N,N-dimethylformamide were added and stirred to obtain a solution. The solution was added with 89.0 g (0. 644 mol) of potassium carbonate, heated to 130° C. and stirred for 3hours. After cooled to room temperature, the reaction mixture was extracted with ethyl acetate and washed with water. Then, the organic layer was separated and dried over anhydrous magnesium sulfate. The solvent was evaporated under reduced pressure to obtain 71.95 g (89%) of Compound (N-8-B).

(Synthesis of Compound (N-8-C))

To a 1-L three-neck flask provided with a stirrer and a reflux condenser, 35.0 g (0.625 mol) of reduced iron, 500 mL of isopropyl alcohol, 100 mL of water and 3.4 g (0.063 mol) of ammonium chloride and refluxed by heating at 90° C. with stirring. To this reaction mixture, the obtained Compound (N-8-B) was gradually added and heated with stirring for 2 hours under the same condition. The hot reaction mixture was filtered through a Cerite layer and washed with ethyl acetate. The filtrate was extracted with ethyl acetate and washed with water, and then the organic layer was separated and dried over anhydrous magnesium sulfate. The solvent was evaporated under reduced pressure to obtain 55.35 g (91%) of Compound (N-8-C).

(Synthesis of Compound N-8)

To a 500-mL three-neck flask provided with a stirrer, 5.64 g (12 mmol) of the obtained Compounds (N-8-C), 200 mL of methyl ethyl ketone, 1.11 g (6 mmol) of cyanuryl chloride and 3.32 g (24 mmol) of potassium carbonate were added and stirred at room temperature for 6 hours under a nitrogen flow. The reaction mixture was filtered through a Cerite layer, and the solvent was evaporated under reduced pressure to obtain 5.6 g (90%) of Compound N-8.

$^1$H NMR (300 MHz, CDCl$_3$): d 7.4–6.8 (m, 6H), 4.10 (m, 8R), 3.85 (m, 8H), 3.70 (m, 8H), 3.60 (m, 8H), 3.45 (m, 8H), 1.55 (m, 8H) 1.30 (m, 12H), 0.85 (t, 12H)

In Synthesis Example for Compound (N-8) mentioned above, an alkyl alcohol having a straight or branched chain, a halogenide thereof or an acid chloride thereof can be used instead of diethylene glycol monohexyl ether to prepare a compound having a straight or branched alkyl group as the terminal side chain. Further, by using an alcohol containing a fluorine atom, a halogenide thereof or an acid chloride thereof, a compound having an alkyl group containing a fluorine atom as the terminal side chain can be prepared.

Furthermore, another heterocyclic compound containing a halogen can be used instead of triazine to prepare a compound containing another heterocyclic group.

[Synthesis Example for Compound S-8]

Compound S-8 was synthesized according to the following synthetic scheme.

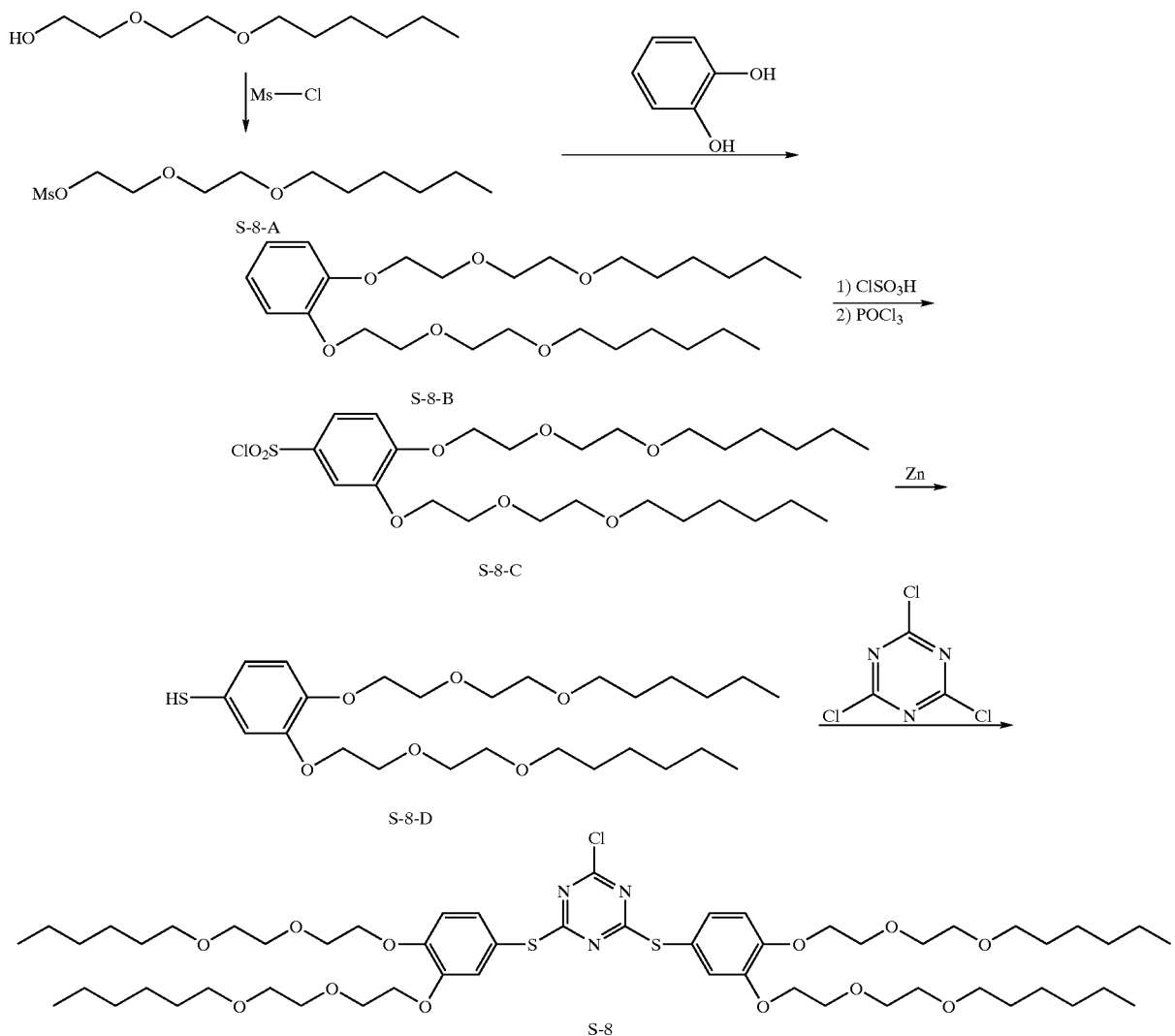

(Synthesis of Compound (S-8-A))

To a 500-mL three-neck flask provided with a stirrer, 95.1 g (0.5 mol) of diethylene glycol monohexyl ether, 150 mL of tetrahydrofuran and 76.7 mL (0.55 mol) of triethylamine were added and stirred to obtain a solution. The solution was cooled to −5° C., and added dropwise with 38.7 mL (0.5 mol) of methanesulfonyl chloride with stirring the solution. After completion of the addition, the reaction mixture was stirred at room temperature for 2 hours. The reaction mixture was extracted with ethyl acetate and washed with water. Then, the organic layer was separated and dried over anhydrous magnesium sulfate. The solvent was evaporated under reduced pressure to obtain 133.8 g (99.7%) of Compound (S-8-A).

(Synthesis of Compound (S-8-B))

To a 500-mL three-neck flask provided with a stirrer, 5.2 g (47.2 mmol) of catechol and 150 mL of N,N-dimethylformamide were added and stirred to obtain a solution. The solution was added with 4.0 g (10.1 mmol) of sodium hydride (60% in oil) with stirring the solution. The solution was added dropwise with 30.0 g (112 mmol) of the obtained Compound (S-8-A) with stirring the solution. After completion of the addition, the reaction mixture was heated to 110° C. and stirred for 1 hour. The reaction mixture was cooled to room temperature, extracted with ethyl acetate and washed with water. Then, the organic layer was separated and dried over anhydrous magnesium sulfate. The solvent was evaporated under reduced pressure to obtain 21.0 g (99%) of Compound (S-8-B).

(Synthesis of Compound (S-8-C))

To a 500-mL three-neck flask provided with a stirrer, 21.0 g (47.0 mmol) of the obtained Compound (S-8-B) and 50 mL of methylene chloride were added and stirred to obtain a solution. The solution was cooled to −10° C., added dropwise with a solution obtained by dissolving 6.27 mL (94 mmol) of chlorosulfonic acid in 10 mL of methylene chloride with stirring the solution. After completion of the addition, the reaction mixture was stirred at room temperature for 1 hour. The reaction mixture was cooled to −10° C., added with 45 mL of acetonitrile and 15 mL of N,N-dimethylacetamide and stirred to obtain a solution. The reaction mixture was added dropwise with 11.0 mL (118 mmol) of phosphorus oxychloride with stirring the solution. After completion of the addition, the reaction mixture was stirred at room temperature for 2 hours. The reaction mixture was extracted with ethyl acetate and washed with water. Then, the organic layer was separated and dried over anhydrous magnesium sulfate. The solvent was evaporated under reduced pressure to obtain 21 g (80.7%) of Compound (S-8-C).

(Synthesis of Compound (S-8-D))

To a 300-mL three-neck flask provided with a stirrer, 7.5 mL of concentrated sulfuric acid and 47 mL of water were added, and the solution was cooled to −10° C. and added with 10.0 g (18.1 mmol) of the obtained Compound (S-8-C). To this solution, 7.45 g (113.9 mmol) of zinc was slowly added. The reaction mixture was refluxed by heating to 90° C. with stirring, and the heating and stirring were continued for 2 hours under the same condition. The hot reaction mixture was filtered through a Cerite layer and washed with ethyl acetate. The filtrate was extracted with ethyl acetate and washed with water, and then the organic layer was separated and dried over anhydrous magnesium sulfate. The solvent was evaporated under reduced pressure to obtain 8.3 g (94%) of Compound (S-8-D).

(Synthesis of Compound (S-8))

To a 100-mL three-neck flask provided with a stirrer and a reflux condenser, 4.0 g (8.2 mmol) of the obtained Compounds (S-8-D) and methyl ethyl ketone were added and stirred to obtain a solution. The solution was added with 0.63 g (3.4 mmol) of cyanuryl chloride and 1.13 g (8.2 mmol) of potassium carbonate and stirred at 70° C. for 1 hour under a nitrogen flow. The reaction mixture was cooled to room temperature, then filtered through a Cerite layer and washed with ethyl acetate. The solvent was evaporated under reduced pressure to obtain 2.95 g (80%) of Compound (S-8).

$^1$H NMR (300 MHz, CDCl$_3$) d 7.0–6.8 (m, 6H), 4.2–4.0 (m, 8H), 3.85 (m, 8H), 3.70 (m, 8H), 3.60 (m, 8H), 3.45 (m, 8H), 1.55 (m, 8H) 1.25 (m, 12H), 0.85 (t, 12H)

In Synthesis Example for Compound (S-8) mentioned above, an alkyl alcohol having a straight or branched chain, a halogenide thereof or an acid chloride thereof can be used instead of diethylene glycol monohexyl ether to prepare a compound having a straight or branched alkyl group as the terminal side chain. Further, by using an alcohol containing a fluorine atom, a halogenide thereof or an acid chloride thereof, a compound having an alkyl group containing a fluorine atom as the terminal side chain can be prepared.

Furthermore, another heterocyclic compound containing a halogen can be used instead of triazine to prepare a compound containing another heterocyclic group.

[Synthesis Example for Compound (N-7)]

Compound (N-7) was obtained in the same manner as in Synthesis Example for Compound (N-8) mentioned above except that isohexyldecane bromide was used instead of Compound (N-8-A)

$^1$H NMR (300 MHz, CDCl$_3$): d 7.4–6.8 (m, 6H), 4.00 (m, 8H), 1.80 (m, 4H), 1.60–1.10 (m, 96H), 0.90 (m, 24H)

[Synthesis Example for Compound (S-7)]

Compound (S-7) was obtained in the same manner as in Synthesis Example for Compound (S-8) mentioned above except that isohexyldecane bromide was used instead of Compound (S-8-A).

$^1$H NMR (300 MHz, CDCl$_3$): d 7.0–6.8 (m, 6H), 4.00 (m, 8H), 1.80 (m, 4H), 1.60–1.10 (m, 96H), 0.90 (m, 24H)

Lubricants of Examples 1 to 12 and Comparative Examples 1 to 4 were prepared by using Compounds N-7, N-8, S-7, S-8, N-34, and S-34 as compounds of the present invention and lubricant base oils. Further, the lubricants were subjected to reciprocating type (SRV) friction wear test in order to evaluate friction coefficient and wear resistance under the test conditions listed below.

[Test Conditions and Measurement Method for Reciprocal Vibration Type (SRV) Friction Wearing Test]

Test Conditions

Specimen (friction material): SUJ-2
  Plate: 24 mm in diameter, 7.9 mm thick
  Cylinder 11 mm in diameter, 15 mm long
  Temperature: 150° C.
  Load: 50 N or 400 N
  Amplitude: 1.0 mm
  Frequency: 50 Hz
  Testing period: for 5 min. after the start of testing The friction coefficients were measured under the test conditions listed in the above under 50 N and 400 N, respectively. The wear resistance was assessed by measuring depth of wear-caused scars using a surface roughness gauge. Results for Examples 1 to 12 were shown in Table 1, and those for Comparative Examples 1 to 4 in Table 2.

TABLE 1

| | | Example 1 | Example 2 | Example 3 | Example 4 | Example 5 | Example 6 | Example 7 | Example 8 | Example 9 | Example 10 | Example 11 | Example 12 |
|---|---|---|---|---|---|---|---|---|---|---|---|---|---|
| Compound of the present invention | Kind | N-7 | N-8 | S-7 | S-8 | N-34 | S-34 | N-7 | N-8 | S-7 | S-8 | N-34 | S-34 |
| | Weight % | 100 | 100 | 100 | 100 | 100 | 100 | 10 | 10 | 10 | 10 | 10 | 10 |
| Lubricant base oil (weight %) | Pentaerythritol ester*1 | — | — | — | — | — | — | 90 | — | — | — | — | — |
| | Alkylbenzene*2 | — | — | — | — | — | — | — | 90 | — | — | — | — |
| | Naphthene type mineral oil | — | — | — | — | — | — | — | — | 90 | — | — | — |
| | Paraffin type mineral oil | — | — | — | — | — | — | — | — | — | 90 | 90 | 90 |
| SRV friction wearing test (@ 50N, 150° C.) | Friction coefficient | 0.03 | 0.02 | 0.03 | 0.02 | 0.02 | 0.02 | 0.08 | 0.07 | 0.08 | 0.07 | 0.06 | 0.06 |
| | Depth of wearing trace (μm) | 0.0 | 0.0 | 0.0 | 0.0 | 0.0 | 0.0 | 0.0 | 0.0 | 0.0 | 0.0 | 0.0 | 0.0 |
| SRV friction | Friction coefficient | 0.04 | 0.03 | 0.04 | 0.03 | 0.025 | 0.025 | 0.09 | 0.08 | 0.09 | 0.08 | 0.07 | 0.07 |

TABLE 1-continued

|  |  | Example 1 | Example 2 | Example 3 | Example 4 | Example 5 | Example 6 | Example 7 | Example 8 | Example 9 | Example 10 | Example 11 | Example 12 |
|---|---|---|---|---|---|---|---|---|---|---|---|---|---|
| wearing test (@ 400N, 150° C.) | Depth of wearing trace (μm) | 0.0 | 0.0 | 0.0 | 0.0 | 0.0 | 0.0 | 0.0 | 0.0 | 0.0 | 0.0 | 0.0 | 0.0 |

*1Hexanoic acid pentaerythritol ester
*2Alkylbenzene having alkyl group containing 10 carbon atoms

TABLE 2

|  |  | Comparative Example 1 | Comparative Example 2 | Comparative Example 3 | Comparative Example 4 |
|---|---|---|---|---|---|
| Lubricant base oil (weight %) | Pentaerythritol ester*1 | 100 | — | — | — |
|  | Alkylbenzene*2 | — | 100 | — | — |
|  | Naphthene type mineral oil | — | — | 100 | — |
|  | Paraffin type mineral oil | — | — | — | 100 |
| SRV friction wearing test (@ 50N, 150° C.) | Friction coefficient | 0.20 | 0.21 | 0.24 | 0.21 |
|  | Depth of wearing trace (μm) | 0.7 | 0.6 | 0.8 | 0.7 |
| SRV friction wearing test (@ 400N, 150° C.) | Friction coefficient | 0.21 | 0.22 | 0.24 | 0.21 |
|  | Depth of wearing trace (μm) | 0.7 | 0.6 | 0.8 | 0.7 |

*1Hexanoic acid pentaerythritol ester
*2Alkylbenzene having alkyl group containing 10 carbon atoms Having described our invention as related to the present embodiments, it is our intention that the invention not be limited by any of the details of the description, unless otherwise specified, but rather be construed broadly within its spirit and scope as set out in the accompanying claims.

What is claimed is:

1. A heterocyclic ring-containing compound represented by the following formula (2):

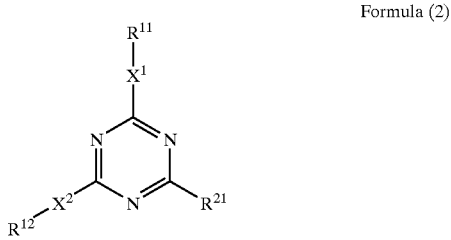

Formula (2)

in the formula, $X^1$ and $X^2$ each independently represent a divalent linking group consisting of a single bond, $NR^3$ group wherein $R^3$ represents a hydrogen atom or an alkyl group having 1–30 carbon atoms, an oxygen atom, a sulfur atom, a carbonyl, a sulfonyl or a combination thereof, $R^{11}$ and $R^{12}$ each independently represent an alkyl group, an alkenyl group, an alkynyl group, an aryl group or a heterocyclic group, which may be substituted or unsubstituted, and at least one of $R^{11}$ and $R^{12}$ contains —(C=O)O—; and $R^{21}$ represents a halogen atom, a hydroxy, an unsubstituted amino, a mercapto, a cyano, a sulfide, a carboxy or salt thereof, a sulfa or salt thereof, a hydroxyamino, a ureido or a urethane.

2. The heterocyclic ring-containing compound of claim 1, wherein, in the formula (2), $X^1$ and $X^2$ represent a sulfur atom or an imino (—NH—).

3. The heterocyclic ring-containing compound of claim 1, wherein, in the formula (2), $X^1$ and $X^2$ represent imino (—NH—).

4. The heterocyclic ring-containing compound of claim 1, wherein, in the formula (2), $X^1$ and $X^2$ represent sulfur atom.

5. The heterocyclic ring-containing compound of claim 1, wherein, in the formula (2), $R^{21}$ represents a halogen atom.

6. The heterocyclic ring-containing compound of claim 2, wherein, in the formula (2), $R^{21}$ represents a halogen atom.

7. The heterocyclic ring-containing compound of claim 3, wherein, in the formula (2), $R^{21}$ represents a halogen atom.

8. The heterocyclic ring-containing compound of claim 1, which is represented by the following formula (3):

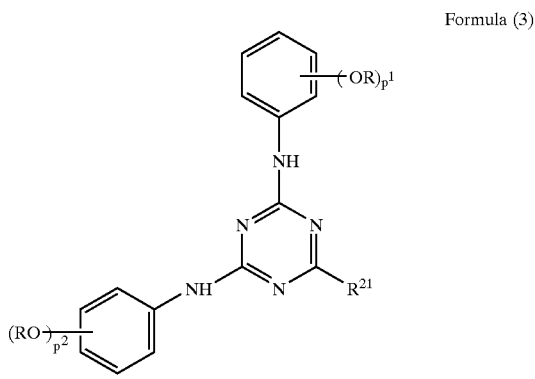

Formula (3)

in the formula, R represents an alkyl group having 8 or more carbon atoms, an oligoalkyleneoxy group having 4 or more carbon atoms or a perfluoroalkyl group having 2 or more carbon atoms, and at least one of R contains —(C=O)O—; $R^{21}$ represents a halogen atom, a hydroxy, an unsubstituted amino, a mercapto, a cyano, a sulfide, a carboxy or salt thereof, a sulfo or salt thereof, a hydroxyamino, a ureido or a urethane, and $p^1$ and $p^2$ each independently represent 1 or 2.

9. A heterocyclic ring-containing compound represented by the following formula (4):

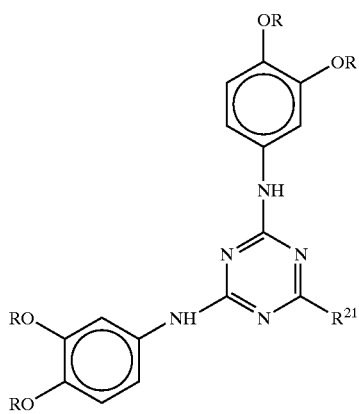

Formula (4)

in the formula, R represents an alkyl group having 8 or more carbon atoms, an oligoalkyleneoxy group having 4 or more carbon atoms or a perfluoroalkyl group having 2 or more carbon atoms, and $R^{21}$ represents a halogen atom, a hydroxy, an unsubstituted amino, a mercapto, a cyano, a sulfide, a carboxy or salt thereof, a sulfo or salt thereof, a hydroxyamino, a ureido or a urethane.

10. The heterocyclic ring-containing compound of claim 8, which is represented by the following formula (5):

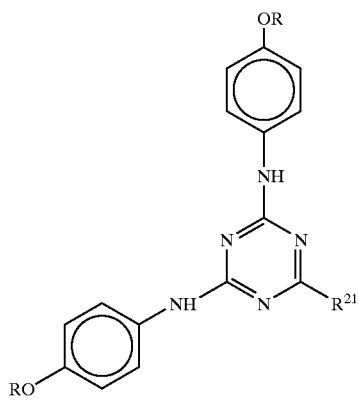

Formula (5)

in the formula, R represents an alkyl group having 8 or more carbon atoms, an oligoalkyleneoxy group having 4 or more carbon atoms or a perfluoroalkyl group having 2 or more carbon atoms, and at least one of R contains —C(C=O)O—; and $R^{21}$ represents a halogen atom, a hydroxy, an unsubstituted amino, a mercapto, a cyano, a sulfide, a carboxy or salt thereof, a sulfo or salt thereof, a hydroxyamino, a ureido or a urethane.

11. A heterocyclic ring-containing compound represented by the following formula (6):

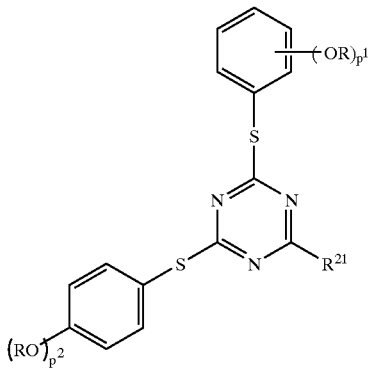

Formula (6)

in the formula, R represents an alkyl group having 8 or more carbon atoms, an oligoalkyleneoxy group having 4 or more carbon atoms or a perfluoroalkyl group having 2 or more carbon atoms, $R^{21}$ represents a halogen atom, a hydroxy, an unsubstituted amino, a mercapto, a cyano, a sulfide, a carboxy or salt thereof, a sulfo or salt thereof, a hydroxyamino, a ureido or a urethane, and $p^1$ and $p^2$ each independently represent 1 or 2.

12. The heterocyclic ring-containing compound of claim 11, which is represented by the following formula (7):

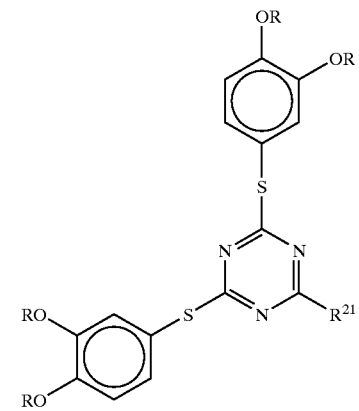

Formula (7)

in the formula, R represents an alkyl group having 8 or more carbon atoms, an oligoalkyleneoxy group having 4 or more carbon atoms or a perfluoroalkyl group having 2 or more carbon atoms, and $R^{21}$ represents a halogen atom, a hydroxy, an unsubstituted amino, a mercapto, a cyano, a sulfide, a carboxy or salt thereof, a sulfo or salt thereof, a hydroxyamino, a ureido or a urethane.

13. The heterocyclic ring-containing compound of claim 11, which is represented by the following formula (8):

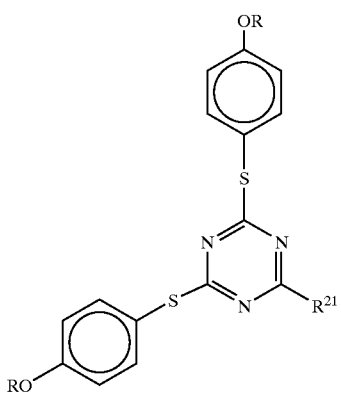

Formula (8)

in the formula, R represents an alkyl group having 8 or more carbon atoms, an oligoalkyleneoxy group having 4 or more carbon atoms or a perfluoroalkyl group having 2 or more carbon atoms, and $R^{21}$ represents a halogen atom, a hydroxy, an unsubstituted amino, a mercapto, a cyano, a sulfide, a carboxy or salt thereof, a sulfo or salt thereof, a hydroxyamino, a ureido or a urethane.

14. A lubricant composition comprising a heterocyclic ring-containing compound represented by the following formula (2):

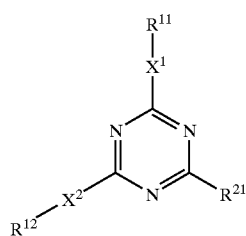

Formula (2)

in the formula, $X^1$ and $X^2$ each independently represent a divalent linking group consisting of a single bond, $NR^3$ group wherein $R^3$ represents a hydrogen atom or an alkyl group having 1–30 carbon atoms, an oxygen atom, a sulfur atom, a carbonyl, a sulfonyl or a combination thereof, $R^{11}$ and $R^{12}$ each independently represent an alkyl group, an alkenyl group, an alkynyl group, an aryl group or a heterocyclic group, which may be substituted or unsubstituted, and at least one of $R^{11}$ and $R^{12}$ contains —(C=O)O—; and $R^{21}$ represents a halogen atom, a hydroxy, an unsubstituted amino, a mercapto, a cyano, a sulfide, a carboxy or salt thereof, a sulfo or salt thereof, a hydroxyamino, a ureido or a urethane.

15. The lubricant composition of claim 14, further comprising a lubricant base oil.

16. The lubricant composition of claim 14, wherein, in the formula (2), $X^1$ and $X^2$ represent a sulfur atom or an imino (—NH—).

17. The lubricant composition of claim 14, wherein, in the formula (2), $X^1$ and $X^2$ represent imino (—NH—).

18. The lubricant composition of claim 14, wherein, in the formula (2), $R^{21}$ represents a halogen atom.

19. The lubricant composition of claim 14, wherein the heterocyclic ring-containing compound is represented by the following formula (3):

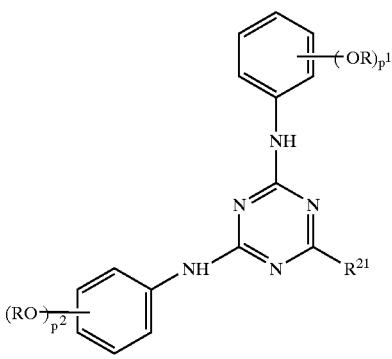

Formula (3)

in the formula, R represents an alkyl group having 8 or more carbon atoms, an oligoalkyleneoxy group having 4 or more carbon atoms or a perfluoroalkyl group having 2 or more carbon atoms, and at least one or R contains —(C=O)O—; $R^{21}$ represents a halogen atom, a hydroxy, an unsubstituted amino, a mercapto, a cyano, a sulfide, a carboxy or salt thereof, a sulfo or salt thereof, a hydroxyamino, a ureido or a urethane, and $p^1$ and $p^2$ each independently represent 1 or 2.

20. The lubricant composition of claim 19, further comprising a lubricant base oil.

21. A lubricant composition comprising a heterocyclic ring-containing compound is represented by the following formula (4):

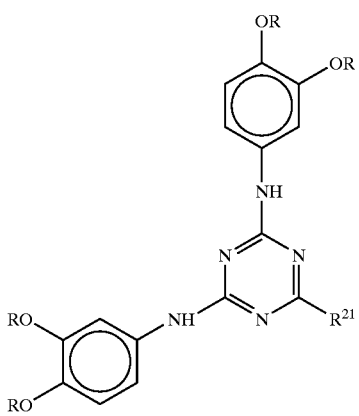

Formula (4)

in the formula, R represents an alkyl group having 8 or more carbon atoms, an oligoalkyleneoxy group having 4 or more carbon atoms or a perfluoroalkyl group having 2 or more carbon atoms, and $R^{21}$ represents a halogen atom, a hydroxy, an unsubstituted amino, a mercapto, a cyano, a sulfide, a carboxy or salt thereof, a sulfo or salt thereof, a hydroxyamino, a ureido or a urethane.

22. The lubricant composition of claim 21, further comprising a lubricant base oil.

* * * * *